United States Patent [19]

Hoehner

[11] 4,403,615

[45] Sep. 13, 1983

[54] THERMAL METHOD FOR MEASURING BLOOD PERFUSION

[76] Inventor: Paul J. Hoehner, 1209 E. Belvedere Ave., Baltimore, Md. 21239

[21] Appl. No.: 330,568

[22] Filed: Dec. 14, 1981

[51] Int. Cl.³ .............................................. A61B 5/08
[52] U.S. Cl. .................................... 128/692; 128/713
[58] Field of Search ................ 128/691, 692, 713, 736

[56] References Cited

U.S. PATENT DOCUMENTS

| 3,915,155 | 10/1975 | Jacobson et al. | 128/2.05 |
| 4,228,805 | 10/1980 | Rosen et al. | 128/691 |
| 4,230,126 | 10/1980 | Elings | 128/713 |

OTHER PUBLICATIONS

Petrofsy, "In Vivo Measurement of Brain Blood Flow in the Cat; IEEE Transactions on Biomedical Engineering," vol. BME-26, No. 8, Aug. 1979.

Ellis et al., "Computerized Monitoring of Cardiac Output by Thermal Dilution"; Journal of the Association of Medical Instrumentation, vol. 6, No. 2, (Mar.-Apr. 1972).

Bourdillion et al., "Saline Conductivity Method for Measuring Cardiac Output Simplified"; Medicol & Biological Engineering and Computing, May 1979, pp. 323-329.

Mendler et al., "Automated Cardiac Output Determination by Indicator Dilution in a Computerized Patient Monitoring System"; Conference: Computers in Cardiology, (Sep. 29, 1977).

Primary Examiner—Richard J. Apley
Assistant Examiner—George Yanulis

[57] ABSTRACT

A thermal method for measuring blood perfusion. One temperature sensor is emplaced in contact with an organ of the patient. Another temperature sensor is inserted in a central artery of the patient. A fluid having a temperature substantially lower then the temperature of the blood of the patient is injected into a vein of the patient. The thermal temperature gradient of the blood perfusion through a portion of the organ in the patient's body is recorded. The thermal temperature gradient of the blood flow through the artery of the patient is also recorded. The area under the curve determined by the thermal temperature gradient of the blood perfusion through the portion of organ of the patient and the area under the curve determined by the thermal temperature gradient of the arterial blood flow are calculated. The difference between the two calculated areas is then determined to provide an indication of the rate of blood perfusion through the portion of the organ in the patient's body.

4 Claims, 2 Drawing Figures

THERMAL METHOD FOR MEASURING BLOOD PERFUSION

BACKGROUND OF THE INVENTION

1. Field of the Invention

This invention relates, in general, to methods for measuring blood perfusion and, more specifically, to thermal methods for measuring blood perfusion.

2. Description of the Prior Art

Recent advances in the understanding of brain death and major neurologic deficit has enhanced interest in the study of cerebral blood flow. As a result, a wide variety of different techniques or methods have been devised to study and measure cerebral blood flow. Some of the more widely known techniques include an inert gas technique, isotopic scanning and the use of radioactive microspheres. Although somewhat effective, all of these methods have a number of disadvantages.

In the inert gas technique, an inert gas, such as nitrous oxide, is inhaled by the patient. The blood flowing out of the brain is then analyzed to measure the inert gas content and provide an indication of the rate of blood flow through the brain. The isotopic scanning technique is somewhat similar and uses a radioactive gas which is traced by a geiger counter as it flows through the brain, with the measured radioactivity providing an indication of cerebral blood flow. Microspheres utilize small glass beads which are radioactively tagged and traced as they flow through the brain.

However, each of these methods measures blood flow through the entire brain and not in a specific region. As it is well known that different regions of the brain have different blood flow rates, such methods are deficient in providing a localized or regional indication of blood flow or blood perfusion through the capillary bed of an organ. In addition, venous pooling and arterial shutdown during major neurological deficit further distort regional blood flow rates which are not detected by these techniques which only measure blood flow through the entire brain.

Another significant disadvantage of these techniques is that do not lend themselves to rapid repetition. Obviously, the amount of radioactive material which is introduced into the body must be carefully controlled in order to prevent harm to the patient. Thus, extended amounts of time must be provided between each measurement segment utilizing these commonly known blood flow measuring techniques. As a result, rapid changes in blood flow rates during surgery or neurological deficit cannot be detected.

Other blood flow measuring techniques have been devised to measure blood flow in other areas of the human body and in particular through the heart. These techniques utilize electro-magnetic flow meters or thermistors which are placed in the arteries to measure the temperature dilution of the blood as cold water is injected into the arteries. In the latter technique, the temperature dilution can be related to blood flow to provide an indication of blood flow through the heart. However, these technique require large vessels, such as arteries or veins, which prevents their use in measuring cerebral blood flow where the arteries and veins are too small for the metering apparatus.

Thus, it would be desirable to provide a method for measuring blood perfusion which overcomes the problems of similar prior art methods. It would also be desirable to provide a method for measuring blood perfusion which may be quickly repeated without danger to the patient. It would also be desirable to provide a method for measuring blood perfusion which provides a measurement of blood perfusion in a particular localized region of an organ of the patient. It would also be desirable to provide a method for measuring blood perfusion which is both simple and inexpensive to use. Finally, it would be desirable to provide a method for measuring blood perfusion which is ideally suited for measuring cerebral blood perfusion.

SUMMARY OF THE INVENTION

There is disclosed herein a unique method for measuring blood perfusion or the rate of flow of blood through the capillary bed of an organ of a patient. According to the method one temperature sensing means is emplaced in contact with an organ of the patient. Another temperature sensing means is inserted in a central artery of the patient. A fluid having a temperature substantially lower than the temperature of the blood of the patient is injected into a vein of the patient. The thermal temperature gradient of the blood perfusion through the portion of the organ in the patient's body is then recorded. The thermal temperature gradient of the blood flow through the artery of the patient is also recorded.

The area under the curve determined by the thermal temperature gradient of the blood perfusion through the portion of the organ of the patient and the area under the curve determined by the thermal temperature gradient of the arterial blood flow are then calculated. Finally, the difference between the two calculated areas is determined to provide an indication of the rate of perfusion of blood through the portion of the organ in the patient's body.

In the preferred embodiment, the fluid which is injected into the body comprises a normal saline solution having a temperature of between 0° C. to about 4° C.

The method of the present invention is especially advantageous for use in measuring cerebral blood perfusion. In this embodiment, the temperature sensing means is inserted through a hole in the skull, past the dura and is emplaced in contact with a region of the brain. In this manner, the thermal temperature gradient of blood perfusion through a region of the brain may be determined.

The method for measuring blood perfusion of the present invention is both simple and inexpensive to use. It lends itself to rapid repetition since no foreign materials which require extended periods of time to be eliminated or washed out of the body are not introduces into the body. Further, the method does not affect vascular resistance since the injectate is physiologically inert and the thermal gradient imposed on the vessel does not exceed 1° C. The method of the present invention also uniquely provides a regional measurement of blood perfusion in a portion of an organ so as to provide specific end organ (capillary bed) perfusion data. In addition, the method of the present invention does not merely provide a measurement of blood flow through one artery; but, measures total blood perfusion from all possible arterial sources.

BRIEF DESCRIPTION OF THE DRAWING

The various features, advantages and other uses of the present invention will become more apparent by referring to the following detailed description and drawing in which.

DESCRIPTION OF THE PREFERRED EMBODIMENTS

Figure 1:
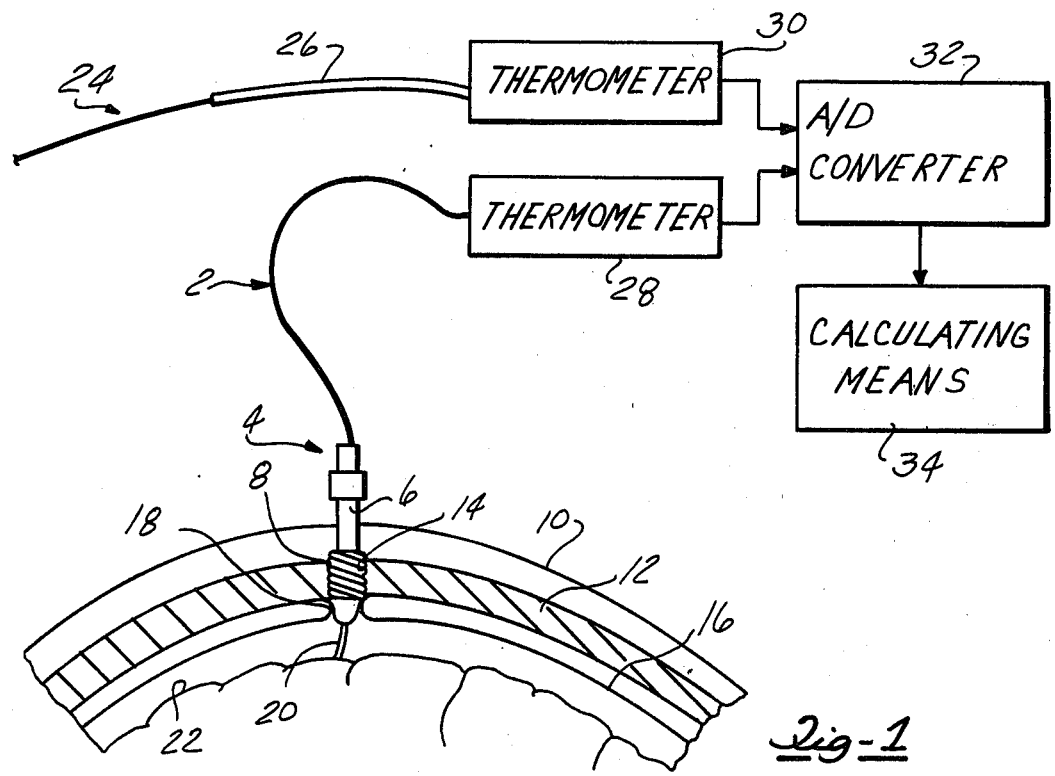
FIG. 1 is a pictorial representation of an apparatus for effecting the method of the present invention when used to measure cerebral blood perfusion.

The method according to the present invention is adapted for measuring blood perfusion in a portion of an organ of a patient. The method comprises the steps of:

a. emplacing one temperature sensing means in contact with an organ of the patient;

b. inserting another temperature sensing means in a central artery of the patient;

c. injecting a fluid having a temperature substantially lower then the temperature of the blood of the patient into a vein of the patient;

d. recording the thermal temperature gradient of the blood perfusion through the organ in the patient's body;

e. recording the thermal temperature gradient of the blood flow through the artery of the patient;

f. calculating the area under the curve determined by the thermal temperature gradient of the blood perfusion through the portion of the organ of the patient;

g. calculating the area under the curve determined by the thermal temperature gradient of the arterial blood flow; and h. determining the difference between the two calculated areas to provide an indication of the rate of blood perfusion through the portion of the organ in the patient's body.

Since the method of the present invention is especially advantageous in measuring cerebral blood perfusion, the following discussion will relate to a description of the use of the present method in conjunction with measuring cerebral blood perfusion. However, it will be understood that the method of the present invention is equally applicable for measuring blood perfusion in other organs of a patient, such as the kidney, liver, heart, etc.

In the preferred embodiment, the first temperature sensing means comprises a thermistor 2 in the form of a thin elongated wire whose resistance changes in proportion to the temperature of the fluid or tissue adjacent its end portion. The thermistor 2 is inserted into the brain of the patient through a head bolt 4. The head bolt 4 includes a shank portion 6 and a threaded portion 8 which securely engages the skull 10 of the patient. In practice, the scalp 10 is reflected bilaterally and the skull 12 exposed. A hole 14 is drilled in the skull to receive the threaded end 8 of the head bolt 4. The dura 14 is carefully opened and the end 18 of the head bolt 4 is inserted therethrough. The thermistor 12 is inserted through a bore in the head bolt 4 until its outermost end 20 contacts the organ, such as the cortex of the brain 22, in which blood flow is desired to be measured. In this manner, approximately one gram of tissue is located in registry with the end 20 of the thermistor 2.

A second temperature sensing means 24 is provided for measuring the temperature of blood flowing into the brain. According to the preferred embodiment, the second temperature sensing means 24 comprises a thermistor 24 which is mounted in a suitably formed catheter 26. The thermistor 24 is inserted using conventional surgical techniques into an artery of the patient. Although any artery may be used, the radial or femoral arteries are preferred. The second thermistor 24 functions to provide an indication of the temperature of the blood flowing through the arteries of the patient prior to its entry into the brain.

Means for recording the temperatures measured by the first and second thermistors 2 and 24 are provided. Preferably, the recording means is in the form of first and second thermometers 28 and 30 to which one end of the first and second thermistors 2 and 24, respectively, are connected. The thermometers 28 and 30 function to convert the resistance changes measured by the first and second thermistors 2 and 24 into electrical signals which are proportional to such resistance changes.

These output signals are input to a conventional A/D converter 32 which converts the analog signals to digital values. The digital values are in turn input to a suitable calculating means 34 which calculates the blood perfusion rate, as described in greater detail hereafter. In the preferred embodiment, the calculating means 34 comprises a conventional digital computer which has been programmed to perform the desired calculations. In addition, it will be understood that an electronic circuit could be devised calibrated to provide a direct indication of the rate of blood perfusion.

According to the next step of the method of the present invention, a cold fluid having a temperature substantially less then the temperature of the blood of the patient is injected into a vein of the patient. The fluid is preferably isotonic in nature so as to have the same concentration of salt as that normally found in the body of the patient. Preferably, a normal saline solution having a salt concentration of 0.9% is utilized.

The temperature of the injected fluid is selected so as to provide an immediate temperature gradient in the blood flow. Preferably, the solution is injected into the vein of the patient at a temperature of about 0° C. to about 4° C. in order to obtain an immediate temperature drop.

It is important that the fluid is injected at a constant rate. Thus, a constant rate infusion pump is preferably utilized. It will be understood, however, that other injecting means, such as an automatic plunger type syringe, may also be used to inject the fluid at a controlled constant rate into the vein of the patient. The volume of fluid injected is selected so as to achieve an immediate 0.5° C. change under the first thermistor 2.

Figure 2:
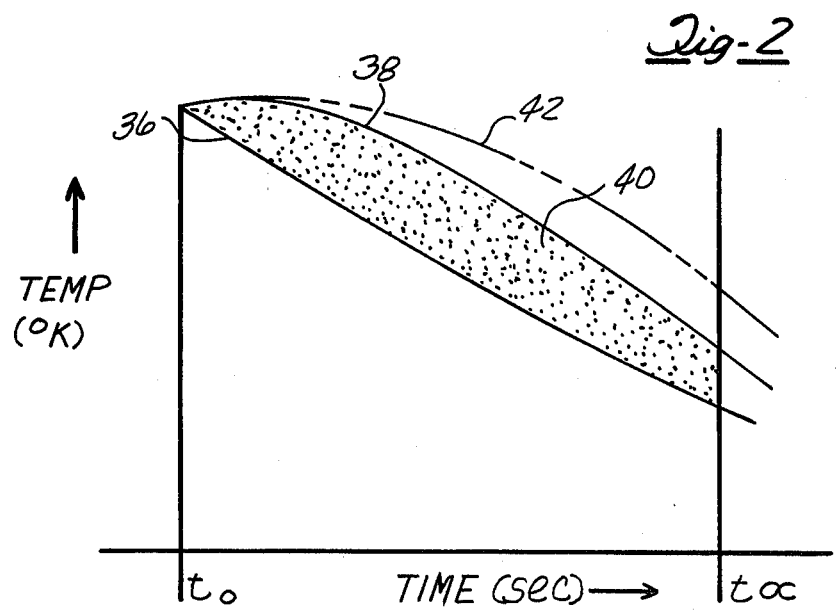
FIG. 2 is a graph depicting the thermal temperature gradient curves measured by the method of the present invention.

The moment that the cold fluid is injected into the body starts the measuring process and is referred to as time zero, $t_o$, as shown in the chart in FIG. 2. Although the measurement period may cover any desired time period, an approximate three minute period is utilized in the preferred embodiment of this invention. During this time period, the thermal temperature gradient of blood perfusion through the one gram of brain tissue is measured by the first thermistor 2 and the thermal temperature gradient of the arterial blood is measured by the second thermistor 24. These values are continually measured and, through the thermometers 28 and 30 and the calculating means 34, two curves 36 and 38 are generated as shown in FIG. 2. The curves 36 and 38 reflect the thermal temperature gradient of blood perfusion through the brain and through the artery of the patient, respectively. As can be seen in the graph in FIG. 2, due to the injection of relatively cold fluid into a vein of the patient, a temperature decrease is noted throughout the measuring time period in which the temperature of the brain tissue and the arterial blood gradually decrease with respect to time.

At the end of the measured time period, the areas under the respective curves 36 and 38 are calculated. This may be effected manually by plotting the curves 36 and 38 and measuring the area underneath or, a calculating means, such as a computer, may be used to sample a series of points along each curve 36 and 38 and calculate the resulting area underneath the curves 36 and 38 according to standard computer programming techniques.

Alternately, standard meters can be calibrated to directly read a blood flow based on the subtracted area. Further, the technician, through experience with the present method, can become sufficiently familiar with the size of the area between the curves 36 and 38 to obtain a reasonably accurate qualitative analysis of the blood perfusion rate merely by observing the curves.

The difference between the areas under the curves 36 and 38, as denoted in general by reference number 40 in FIG. 2, is inversely proportional to the rate of blood perfusion through the portion of an organ of the patient, such as through one gram of brain tissue. In this manner, an indication of the rate of blood perfusion through the portion of an organ of the patient, such as through a localized region of the brain, may be determined. Thus, depending upon the patient's particular condition and physical characteristics, the difference between the areas under curves 36 and 38, as denoted by region 40 in the graph depicted in FIG. 2, may be indicative of good or sufficient blood perfusion in the brain. Similarly, the difference between the area under curve 42 and that under curve 36 may be indicative of poor flow thereby enabling suitable corrective action to be taken to improve the blood perfusion through the brain.

An actual numeric value for the blood perfusion through the measured portion of an organ of the patient may be calculated using equations which incorporate several variables inherent in the measuring technique of the present invention. Such a calculation may be performed manually or may be solved utilizing a conventional digital computer suitably programmed to solve the relatively complex equations described hereafter.

Although the following equations provide a specific numeric value for the blood perfusion through the measured portion of an organ, such equations merely calculate the area in the graph depicted in FIG. 2 underneath each of the curves 36 and 38.

The temperature $T_{Ta}$ at any time ($t_a$) on the curve 36 can be expressed by the equation:

$$T_{Ta} = T_{To} + \left( \frac{t \cdot F_{IV}(T_{IV} - T_{To})}{V_{BO} + F_{IV} \cdot t} \right) - \left( \frac{t \cdot F_{IV} \cdot (T_{IV} - T_{To})}{(t \cdot Q + 1) \cdot (t \cdot F_{IV} + V_{BO})} \right) \quad (1)$$

Integration of this expression $$\left( S_{TTo}^{TTa} T_T dT_T \right)$$

yields the area under the curve 36 which reflects the thermal temperature gradient of blood flow through the measured portion of an organ, such as the brain, and may be given by the equation:

$$\text{Area}_T = (t \cdot T_{IV}) \cdot \left( \frac{V_{BO}^2 \cdot Q^2 \cdot \ln[V_{BO}/(V_{BO} + F_{IV} \cdot t)] + F_{IV}^2 \cdot (\ln[1 + Q \cdot t])}{F_{IV} \cdot Q \cdot (F_{IV} - V_{BO} \cdot Q)} \right) \cdot (T_{IV} - T_{To}) \quad (2)$$

Where:
T=temperature in degrees Kelvin, V=Volume in cc,
F=flow in cc/sec, Q=flow in cc/sec/gm,
t=time in sec, BO- blood out, BI=blood in,
IV=I.V. fluid, subscript T=tissue directly under thermistor 2.

The temperature $T_{BI}$ at any time ($t_a$) on the curve 38 can be expressed by the equation:

$$T_{BI} = T_{IV} + \frac{V_{Bo} \cdot (T_{Bo} - T_{IV})}{V_{Bo} + t \cdot F_{IV}} \quad (3)$$

Integration of this expression $$\left( \int_{t=o}^{t=2} T_{BI} dT_{BJ} \right)$$

yields the area under the curve 38, and may be given by the equation:

$$\text{Area}_B = t \cdot T_{IV} + \left( \frac{V_{Bo}(T_{Bo} - T_{IV})}{F_{IV}} \right) \cdot \ln\left( \frac{V_{Bo} + t \cdot F_{IV}}{V_{Bo}} \right) \quad (4)$$

The difference between the numeric values obtained by solving equations (2) and (4) equals the difference in the areas under the two thermal temperature gradient curves 36 and 38 shown in FIG. 2 which is proportional to the blood perfusion through the portion of the organ, such as the brain. In actual practice, using a suitably programmed digital computer, once the areas under both curves 36 and 38 are calculated, equation (2) is solved for Q, by repeated approximation, to provide a discrete numeric value for the blood perfusion through the measured portion of the organ of the patient.

Thus, there has been disclosed a unique method for measuring blood perfusion in a portion of an organ of a patient which is particularly useful in measuring cerebral blood perfusion. The method is both simple and inexpensive to use and provides a measurement of blood perfusion in a particular localized portion of an organ of the patient. The method of the present invention may be repeated at frequent intervals without harm to the patient and without loss of accuracy.

What is claimed is:

1. A method for measuring blood perfusion comprising the steps of:
   a. emplacing one temperature sensing means in contact with an organ of the patient;
   b. inserting another temperature sensing means in a central artery of the patient;

c. injecting a fluid having a temperature substantially lower than the temperature of the blood of the patient into a vein of the patient;
d. recording the thermal temperature gradient of the blood perfusion through the portion of the organ in the patient's body;
e. recording the thermal temperature gradient of the blood flow through the artery of the patient;
f. calculating the area under the curve determined by the thermal temperature gradient of the blood perfusion through the portion of organ of the patient;
g. calculating the area under the curve determined by the thermal temperature gradient of the arterial blood flow; and
h. determining the difference between the two calculated areas to provide an indication of the rate of blood perfusion through the portion of the organ in the patient's body.

2. The method of claim 1 wherein the fluid is a saline solution.

3. The method of claim 1 wherein the temperature of the injected fluid is between about 0° C. and about 4° C.

4. The method of claim 1 wherein the first temperature sensing means is mounted through the skull of the patient in contact with the brain to provide a measurement of blood perfusion through a particular region of the brain.

* * * * *